United States Patent [19]

Schouteeten et al.

[11] Patent Number: 5,138,096
[45] Date of Patent: Aug. 11, 1992

[54] NEW CONTINUOUS INDUSTRIAL MANUFACTURING PROCESS FOR AN AQUEOUS SOLUTION OF GLYOXYLIC ACID

[75] Inventors: Alain Schouteeten, Ezanville; Jean-Michel Alarcon, Trosly Breuil, both of France

[73] Assignee: Societe Francaise Hoechst, Puteaux, France

[21] Appl. No.: 614,521

[22] Filed: Nov. 16, 1990

[30] Foreign Application Priority Data

Nov. 16, 1989 [FR] France ................................ 89 15036

[51] Int. Cl.$^5$ .................... C07C 51/235; C07C 59/153
[52] U.S. Cl. ...................................... 562/531; 562/577
[58] Field of Search .............................. 562/531, 577

[56] References Cited

U.S. PATENT DOCUMENTS 4,698,441 10/1987 Mitani et al. .................... 562/531

FOREIGN PATENT DOCUMENTS 1002309 2/1957 Fed. Rep. of Germany .

OTHER PUBLICATIONS

Patent Abstracts of Japan, vol. 9, No. 74 (C-273) [1797], Apr. 3, 1985.

*Primary Examiner*—Jose G. Dees
*Assistant Examiner*—B. Frazier
*Attorney, Agent, or Firm*—Browdy and Neimark

[57] ABSTRACT

Continuous manufacturing process for an aqueous solution of glyoxylic acid by nitric oxidation of an aqueous solution of glyoxal carried out in the presence of hydrochloric acid in which the oxidation is effected continuously using 0.80±0.2 mole of nitric acid and 0.70±0.05 mole of hydrochloric acid per mole of glyoxal in a reaction medium having a concentration by weight between 5 and 6% of hydrochloric acid and higher than 10% of nitric acid.

12 Claims, No Drawings

NEW CONTINUOUS INDUSTRIAL MANUFACTURING PROCESS FOR AN AQUEOUS SOLUTION OF GLYOXYLIC ACID

A new industrial manufacturing process for an aqueous solution of glyoxylic acid obviating these disadvantages has now been discovered.

The process according to the present invention which consists of subjecting an aqueous solution of glyoxal to a nitric oxidation in the presence of hydrochloric acid is characterized in that it is carried out continuously in a reaction mixture containing a concentration by weight of nitric acid of greater than 10% and of hydrochloric acid of between 5 and 6% using 0.80±0.02 mole of nitric acid and 0.70±0.05 mole of hydrochloric acid per mole of glyoxal used.

The process of the present invention allows the glyoxal to be converted virtually quantitatively into a mixture of glyoxylic and oxalic acids. The losses of glyoxal are very slight, always less than 1% and the non-converted glyoxal is always less than 2%. As for the nitric acid, it is substantially totally consumed, so well that the aqueous solutions of glyoxylic acid obtained always contain less than 0.1% by weight of residual nitric acid. The selectivity of the oxidation of the glyoxal into glyoxylic acid is between 75 and 80%.

The process according to the present invention is preferably carried out at a temperature between 30° and 80° C. In particular the operation is done at a pressure between 0.5 and 10 bars and advantageously at a pressure between 1 and 5 bars.

The process according to the present invention can be effected for example in a series of reactors agitated in series, or better still, in an assembly constituted by one or more agitated reactors followed by one or more piston reactors.

Advantageously, either three reactors agitated in series, or preferably one agitated reactor followed by two piston reactors are used. The supply of reactors is effected continuously in the first reactor and advantageously the gases resulting from the process are washed with the incoming supply of the aqueous solution of glyoxal. On leaving the last reactor, the reaction mixture is cooled down to ambient temperature, then the oxalic acid formed is eliminated by crystallization and the mother liquors containing the glyoxylic acid formed, the hydrochloric acid and traces of oxalic acid and nitric acid are subjected to two successive electrodialyses which allow the extraction from the reaction medium, firstly of the hydrochloric acid which is recycled, then of the residual oxalic acid which is recycled in the reaction medium resulting from the last reactor.

The reaction medium leaving the second electrodialysis machine is either used as it is, or concentrated under reduced pressure to the desired concentration of glyoxylic acid.

For the supply, commercially available aqueous solutions of glyoxal, of hydrochloric acid and of nitric acid, optionally diluted with water, are preferably used. The oxidation according to the process of the invention is quick: usually it requires less than two hours and it is advantageously effected in successive reactors heated to identical temperatures or to higher and higher temperatures.

Preferably, the oxidation is started at 45° C., then completed at 55° C.

The aqueous solutions of glyoxylic acid are in particular currently used to access vanillin starting with guaiacol or parahydroxymandelic acid starting with phenol.

The following example illustrates the invention without however limiting it.

EXAMPLE

An agitated reactor maintained at 45°±1° C., followed by two piston reactors in series, maintained at 55° C., are supplied continuously with:

29,020 g/h of an aqueous solution of glyoxal at 20% by weight, that is 100 moles/h of glyoxal, 13,322 g/h of hydrochloric acid at 20% by weight, that is 73 moles/h of hydrogen chloride, 7,441 g/h of nitric acid at 69% by weight, that is 81.5 moles/h of nitric acid at 100%.

This reaction mixture remains in the agitated reactor for 12 minutes, then for 35 minutes in the first piston reactor and finally for 45 minutes in the second piston reactor, then the reaction mixture is cooled down. The oxalic acid formed crystallizes and after elimination of the oxalic acid crystals by filtration, the reaction medium is subjected to two successive electrodialyses to eliminate the hydrochloric acid and then the residual oxalic acid. The hydrochloric acid isolated in the first electrodialysis machine is recycled to the start of the process and the aqueous solution of oxalic acid containing traces of hydrochloric acid and glyoxylic acid is recycled on leaving the second piston reactor.

At the exit of the second piston reactor, 47,391 g/h of an aqueous solution containing by weight 12.11% of glyoxylic acid, or 77.5 moles/h, 5.62% of hydrochloric acid, or 73 moles/h, 3.9% of oxalic acid, or 20.5 moles/h, 0.18% of glyoxal, or 1.5 mole/h, 0.04% of nitric acid, or 0.03 mole/h and finally 78.15% of water. At the same time, gases are released which, after washing with the aqueous solution of glyoxal of the beginning of the process, have an output of 2,390 g/h and which are constituted by 92.6% of nitrogen oxide, or 73.8 moles/h, 1.2% of nitrogen, or 1 mole/h, 4.1% of nitrous oxide, or 2.2 moles/h and 2.1% of carbon dioxide, or 1.1 mole/h.

The yield of glyoxylic acid is established at 77-78% relative to the glyoxal used, the yield of oxalic acid is established at 20-21% relative to the glyoxal and only 0.5% of the glyoxal is lost as carbon dioxide.

The conversion rate of the glyoxal is about 98.5%.

On leaving the second electrodialysis machine, the aqueous solution of glyoxylic acid containing minute traces of hydrochloric acid, oxalic acid and nitric acid is concentrated so as to bring its titer to 40% or 50% according to commercial demands.

The 69% nitric acid can be replaced by 55% nitric acid. To do this, it is sufficient to supply the reactor with an aqueous solution either of glyoxal, or of hydrochloric acid, or of these two products slightly more concentrated. Thus, for example, if the reactor is supplied with 81.5 moles/h of 55% nitric acid, or 9,335.5 g/h, 27,126 g/h of a 21.4% aqueous solution of glyoxal, or 100 moles, are used.

We claim:

1. Manufacturing process for an aqueous solution of glyoxylic acid by nitric oxidation of an aqueous solution of glyoxal carried out in the presence of hydrochloric acid, characterized in that this oxidation is effected continuously using 0.80±0.02 mole of nitric acid and 0.70±0.05 mole of hydrochloric acid per mole of glyoxal in a reaction medium which has a concentration by weight between 5 and 6% of hydrochloric acid and higher than 10% of nitric acid.

2. Process according to claim 1, characterized in that is is used at a temperature between 30° and 80° C.

3. Process according to claim 1, characterized in that it is carried out at a pressure between 0.5 and 10 bars.

4. A process for the continuous manufacture of an aqueous solution of glyoxylic acid, comprising:

continuously feeding nitric acid, hydrochloric acid and an aqueous solution of glyoxal to a first of a series of reactors at a rate of 0.80±0.02 mole of nitric acid and 0.70±0.05 mole of hydrochloric acid per mole of glyoxal to provide a reaction medium having a concentration by weight of 5-6% hydrochloric acid and greater than 10% nitric acid;

effecting oxidation of said glyoxal in said series of reactors while feeding said reaction medium through said series of reactors;

withdrawing reaction product from a last of said series of reactors and separating said reaction product into oxalic acid, glyoxylic acid and a small amount of hydrochloric acid.

5. A process according to claim 4 wherein said small amount of hydrochloric acid is recycled, said oxidation being carried out at a temperature between 30° and 80° C.

6. A process according to claim 5 wherein said oxidation is started in said first reactor at about 45° C. and completed in said last reactor at about 55° C.

7. A process according to claim 4 wherein the recovery yield of said glyoxylic acid is at least about 77% relative to the glyoxal, and the yield of said oxalic acid is at least about 20% relative to said glyoxal.

8. A process according to claim 4 wherein the conversion rate of the glyoxal is about 98.5%.

9. A process according to claim 4 wherein said separation of said oxalic acid is effected by cooling the reaction product leaving said last reactor and crystallizing said oxalic acid, said method further comprising passing mother liquor from said crystallization to a purification stage to remove hydrochloric and residual oxalic acid, recycling said hydrochloric acid and passing said residual oxalic acid to the reaction product leaving said last reactor.

10. A process according to claim 5 wherein each of said reactors is maintained at substantially the same temperature.

11. A process according to claim 5 wherein the first of said reactors is maintained at a first temperature and each subsequent reactor is maintained at a slightly greater temperature.

12. A process according to claim 4 wherein the time of passage through said reactor is less than two hours so that oxidation is effected in less than two hours.

* * * * *